US012595315B2

(12) United States Patent
Chang et al.

(10) Patent No.: US 12,595,315 B2
(45) Date of Patent: Apr. 7, 2026

(54) MONOCLONAL ANTIBODY OF MATRIX METALLOPROTEINASE-1, DETECTION KIT AND DETECTION METHOD THEREOF

(71) Applicant: S&T BIOMED CO., LTD., Zhubei City (TW)

(72) Inventors: Ya-Ting Chang, Taoyuan City (TW); Jau-Song Yu, Taoyuan City (TW); Jun-Sheng Wang, Zhubei City (TW); Shu-Fang Wu, Taoyuan City (TW); Chih-Ju Chen, New Taipei City (TW); Yen-Chun Liu, Keelung City (TW)

(73) Assignee: S&T BIOMED CO., LTD., Zhubei City (TW)

( * ) Notice: Subject to any disclaimer, the term of this patent is extended or adjusted under 35 U.S.C. 154(b) by 778 days.

(21) Appl. No.: 17/791,744

(22) PCT Filed: Feb. 27, 2020

(86) PCT No.: PCT/CN2020/076960
§ 371 (c)(1),
(2) Date: Jul. 8, 2022

(87) PCT Pub. No.: WO2021/168734
PCT Pub. Date: Sep. 2, 2021

(65) Prior Publication Data
US 2023/0192888 A1 Jun. 22, 2023

(51) Int. Cl.
*C07K 16/40* (2006.01)
*G01N 33/543* (2006.01)

(52) U.S. Cl.
CPC ....... *C07K 16/40* (2013.01); *G01N 33/54387* (2021.08); *C07K 2317/565* (2013.01)

(58) Field of Classification Search
CPC .............. C07K 16/40; C07K 2317/565; G01N 33/54387
See application file for complete search history.

(56) References Cited

U.S. PATENT DOCUMENTS

| | | | | |
|---|---|---|---|---|
| 7,550,562 | B2 * | 6/2009 | Tsunoda | A61K 38/177 530/350 |
| 9,409,995 | B2 * | 8/2016 | Foord | C07K 16/40 |
| 2009/0191543 | A1 | 7/2009 | Radisky et al. | |
| 2015/0110791 | A1 * | 4/2015 | Zhang | A61P 31/12 435/69.6 |

FOREIGN PATENT DOCUMENTS

| | | |
|---|---|---|
| CN | 102445543 A | 5/2012 |
| CN | 109725146 A | 5/2019 |
| EP | 3366704 A1 | 8/2018 |
| JP | 2009538877 A | 11/2009 |
| JP | 2010538244 A | 12/2010 |
| TW | 201734455 A | 10/2017 |
| WO | WO-2018136553 A1 * | 7/2018 ......... C07K 16/2827 |
| WO | 2019224210 A1 | 11/2019 |

OTHER PUBLICATIONS

Caulfield MJ, Stanko D. A pathogenic monoclonal antibody, G8, is characteristic of antierythrocyte autoantibodies from Coombs'-positive NZB mice. J Immunol. Apr. 1, 1992;148(7):2068-73. PMID: 1545119. (Year: 1992).*

Takahashi Y, Ohta H, Takemori T. Fas is required for clonal selection in germinal centers and the subsequent establishment of the memory B cell repertoire. Immunity. Feb. 2001;14(2):181-92. doi: 10.1016/s1074-7613(01)00100-5. PMID: 11239450. (Year: 2001).*

Almagro JC, Fransson J. Humanization of antibodies. Front Biosci. Jan. 1, 2008;13:1619-33. doi: 10.2741/2786. PMID: 17981654. (Year: 2008).*

Shao W, Hu F, Ma J, Zhang C, Liao Q, Zhu Z, Liu E, Qiu X. Epithelial cells are a source of natural IgM that contribute to innate immune responses. Int J Biochem Cell Biol. Apr. 2016;73:19-29. doi: 10.1016/j.biocel.2016.01.017. Epub Jan. 25, 2016. PMID: 26820901. (Year: 2016).*

Hasegawa H, et al. Single amino acid substitution in LC-CDR1 induces Russell body phenotype that attenuates cellular protein synthesis through eIF2α phosphorylation and thereby downregulates IgG secretion despite operational secretory pathway traffic. MAbs. Jul. 2017;9(5):854-873. (Year: 2017).*

Banihashemi SR, Hosseini AZ, Rahbarizadeh F, Ahmadvand D. Development of specific nanobodies (VHH) for CD19 immuno-targeting of human B-lymphocytes. Iran J Basic Med Sci. May 2018;21(5):455-464. doi: 10.22038/IJBMS.2018.26778.6557. PMID: 29922424; PMCID: PMC6000210. (Year: 2018).*

Wagner, H.J.; Wehrle, S.; Weiss, E.; Cavallari, M.; Weber, W. A Two-Step Approach for the Design and Generation of Nanobodies. Int. J. Mol. Sci. 2018, 19, 3444. https://doi.org/10.3390/ijms19113444 (Year: 2018).*

Chiu ML, Goulet DR, Teplyakov A, Gilliland GL. Antibody Structure and Function: The Basis for Engineering Therapeutics. Antibodies (Basel). Dec. 3, 2019;8(4):55. doi: 10.3390/antib8040055. PMID: 31816964; PMCID: PMC6963682. (Year: 2019).*

Fan, H-X. et al., "Expression of MMP-1/PAR-1 and patterns of invasion in oral squamous cell carcinoma as potential prognostic markers", OncoTargets and Therapy, 8, doi: 10.2147/OTT.S84561, Jul. 3, 2015, 1619-1626.

(Continued)

*Primary Examiner* — Melenie L Gordon
*Assistant Examiner* — John Paul Selwanes
(74) *Attorney, Agent, or Firm* — CKC & Partners Co., LLC

(57) ABSTRACT

Provided is a monoclonal antibody of matrix metalloproteinase 1. The monoclonal antibody has a heavy chain variable region with an amino sequence comprising i) CDR1 selected from the group consisting of SEQ ID NOs: 1, 7 and 13, ii) CDR2 selected from the group consisting of SEQ ID NOs: 2, 8 and 14, and iii) CDR3 selected from the group consisting of SEQ ID NOs: 3, 9 and 15. The monoclonal antibody also has a light chain variable region with an amino sequence comprising i) CDR1 selected from the group consisting of SEQ ID NOs: 4, 10 and 16, ii) CDR2 selected from the group consisting of SEQ ID NOS: 5, 11 and 17, and iii) CDR3 selected from the group consisting of SEQ ID NOs: 6, 12 and 18. A polynucleotide, a detection kit and a detection method are also provided as well.

12 Claims, 6 Drawing Sheets

Specification includes a Sequence Listing.

(56) References Cited

OTHER PUBLICATIONS

Anonymous , "MMP1 Gene", GeneCards; MMP1 Protein; MMP1 Antibody. Retrieved from the Internet: URL:https://web.archive. org/web20190908095636/https://www.genecards.org/cgi-bin/carddisp. pl?gene=MMP1, retrieved on Oct. 23, 2023, Sep. 8, 2019, 18 pgs.

* cited by examiner

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial Sequence
<220> FEATURE:
<221> NAME/KEY: V_segment
<223> OTHER INFORMATION: CDR1 of heavy chain variable region sequence of
      monoclonal antibody 31-34

<400> SEQUENCE: 1

Gly Tyr Ser Phe Thr Asp Tyr Ile Met Leu
1               5                   10

<210> SEQ ID NO 2
<211> LENGTH: 17
<212> TYPE: PRT
<213> ORGANISM: Artificial Sequence
<220> FEATURE:
<221> NAME/KEY: V_segment
<223> OTHER INFORMATION: CDR2 of heavy chain variable region sequence of
      monoclonal antibody 31-34
```

```
<400> SEQUENCE: 2

Asn Ile Asn Pro His Tyr Gly Gly Thr Ser Tyr Asn Leu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: V_segment
<223> OTHER INFORMATION: CDR3 of heavy chain variable region sequence of
      monoclonal antibody 31-34

<400> SEQUENCE: 3

Ala Arg Tyr Gly Phe Ser Ala Trp Phe Ala Tyr
1               5                   10

<210> SEQ ID NO 4
<211> LENGTH: 11
<212> TYPE: PRT
<213> ORGANISM: Artificial Sequence
<220> FEATURE:
<221> NAME/KEY: V_segment
<223> OTHER INFORMATION: CDR1 of light chain variable region sequence of
      monoclonal antibody 31-34

<400> SEQUENCE: 4

Arg Ala Ser Glu Asn Ile Tyr Ser Asn Leu Ala
1               5                   10

<210> SEQ ID NO 5
<211> LENGTH: 7
<212> TYPE: PRT
<213> ORGANISM: Artificial Sequence
<220> FEATURE:
<221> NAME/KEY: V_segment
<223> OTHER INFORMATION: CDR2 of light chain variable region sequence of
      monoclonal antibody 31-34

<400> SEQUENCE: 5

Ala Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: V_segment
<223> OTHER INFORMATION: CDR3 of light chain variable region sequence of
      monoclonal antibody 31-34

<400> SEQUENCE: 6

Gln His Phe Trp Gly Ile Pro Phe Thr
1               5

<210> SEQ ID NO 7
<211> LENGTH: 7
<212> TYPE: PRT
<213> ORGANISM: Artificial Sequence
<220> FEATURE:
<221> NAME/KEY: V_segment
<223> OTHER INFORMATION: CDR1 of heavy chain variable region sequence of
      monoclonal antibody 73-1

<400> SEQUENCE: 7
```

-continued

```
Gly Tyr Thr Phe Ser Asn Tyr
1               5

<210> SEQ ID NO 8
<211> LENGTH: 17
<212> TYPE: PRT
<213> ORGANISM: Artificial Sequence
<220> FEATURE:
<221> NAME/KEY: V_segment
<223> OTHER INFORMATION: CDR2 of heavy chain variable region sequence of
      monoclonal antibody 73-1

<400> SEQUENCE: 8

Glu Ile Leu Pro Gly Gly Gly Asn Thr Tyr His Asn Glu Lys Phe Lys
1               5                   10                  15

Gly

<210> SEQ ID NO 9
<211> LENGTH: 13
<212> TYPE: PRT
<213> ORGANISM: Artificial Sequence
<220> FEATURE:
<221> NAME/KEY: V_segment
<223> OTHER INFORMATION: CDR3 of heavy chain variable region sequence of
      monoclonal antibody 73-1

<400> SEQUENCE: 9

Ala Arg Ser Gly Asp Asp Tyr Asp Asp Val Phe Ala Tyr
1               5                   10

<210> SEQ ID NO 10
<211> LENGTH: 15
<212> TYPE: PRT
<213> ORGANISM: Artificial Sequence
<220> FEATURE:
<221> NAME/KEY: V_segment
<223> OTHER INFORMATION: CDR1 of light chain variable region sequence of
      monoclonal antibody 73-1

<400> SEQUENCE: 10

Arg Ala Ser Glu Ser Val Asp Ser His Gly Lys Thr Phe Met His
1               5                   10                  15

<210> SEQ ID NO 11
<211> LENGTH: 7
<212> TYPE: PRT
<213> ORGANISM: Artificial Sequence
<220> FEATURE:
<221> NAME/KEY: V_segment
<223> OTHER INFORMATION: CDR2 of light chain variable region sequence of
      monoclonal antibody 73-1

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<221> NAME/KEY: V_segment
<223> OTHER INFORMATION: CDR3 of light chain variable region sequence of
      monoclonal antibody 73-1

<400> SEQUENCE: 12

Gln Gln Ser Asn Glu Asp Pro Trp Thr
1               5
```

```
<210> SEQ ID NO 13
<211> LENGTH: 7
<212> TYPE: PRT
<213> ORGANISM: Artificial Sequence
<220> FEATURE:
<221> NAME/KEY: V_segment
<223> OTHER INFORMATION: CDR1 of heavy chain variable region sequence of
      monoclonal antibody 1-8A12

<400> SEQUENCE: 13

Gly Tyr Thr Phe Thr Asn Tyr
1               5

<210> SEQ ID NO 14
<211> LENGTH: 17
<212> TYPE: PRT
<213> ORGANISM: Artificial Sequence
<220> FEATURE:
<221> NAME/KEY: V_segment
<223> OTHER INFORMATION: CDR2 of heavy chain variable region sequence of
      monoclonal antibody 1-8A12

<400> SEQUENCE: 14

Asp Ile Tyr Pro Tyr Ser Gly Thr Thr Asn Tyr Asn Glu Lys Phe Lys
1               5                   10                  15

Ser

<210> SEQ ID NO 15
<211> LENGTH: 12
<212> TYPE: PRT
<213> ORGANISM: Artificial Sequence
<220> FEATURE:
<221> NAME/KEY: V_segment
<223> OTHER INFORMATION: CDR3 of heavy chain variable region sequence of
      monoclonal antibody 1-8A1

<400> SEQUENCE: 15

Ala Arg Asp Glu Ile Thr Ser Pro Tyr Phe Ser Tyr
1               5                   10

<210> SEQ ID NO 16
<211> LENGTH: 11
<212> TYPE: PRT
<213> ORGANISM: Artificial Sequence
<220> FEATURE:
<221> NAME/KEY: V_segment
<223> OTHER INFORMATION: CDR1 of light chain variable region sequence of
      monoclonal antibody 1-8A12

<400> SEQUENCE: 16

Lys Ala Ser Gln Ser Val Gly His Asp Val Ala
1               5                   10

<210> SEQ ID NO 17
<211> LENGTH: 7
<212> TYPE: PRT
<213> ORGANISM: Artificial Sequence
<220> FEATURE:
<221> NAME/KEY: V_segment
<223> OTHER INFORMATION: CDR2 of light chain variable region sequence of
      monoclonal antibody 1-8A12

<400> SEQUENCE: 17

Tyr Ala Ser Asn Arg Tyr Thr
1               5
```

-continued

```
<210> SEQ ID NO 18
<211> LENGTH: 9
<212> TYPE: PRT
<213> ORGANISM: Artificial Sequence
<220> FEATURE:
<221> NAME/KEY: V_segment
<223> OTHER INFORMATION: CDR3 of light chain variable region sequence of
      monoclonal antibody 1-8A12

<400> SEQUENCE: 18

Gln Gln Asp Tyr Ser Ser Pro Trp Thr
1               5
```

MONOCLONAL ANTIBODY OF MATRIX METALLOPROTEINASE-1, DETECTION KIT AND DETECTION METHOD THEREOF

CROSS-REFERENCE TO RELATED APPLICATION

This application is the National Stage Entry of International Application No. PCT/CN2020/076960, filed Feb. 27, 2020, which is herein incorporated by reference.

The Sequence Listing associated with this application is filed in electronic format via EFS-Web and is hereby incorporated by reference into the specification in its entirety. The name of the text file containing the Sequence Listing is NP-26132-US_SEQ_LIST.txt. The size of the text file is 5,518 bytes, and the text file was created on Feb. 21, 2020.

BACKGROUND

Field of Invention

The present disclosure relates to a MMP-1 and a method of detection of oral cancer, and in particular to a MMP-1 monoclonal antibody, a detection kit containing the MMP-1 monoclonal antibody, and a detection method using the detection kit.

Description of Related Art

According to statistics of the World Health Organization, more than 529,000 new cases of oral cancer are diagnosed each year. Due to the increasing incidence rate, the number is expected to reach 856,000 cases per year by 2035. In Taiwan, according to the 2016 death cause statistics from the health promotion administration of the ministry of health and welfare (hereinafter referred to as the health promotion administration), oral cancer, oropharyngeal cancer and hypopharyngeal cancer were the fourth leading cause of death among all male malignant tumors. About 7,000 people are newly diagnosed with the disease each year, and about 3,000 people die. Between 2012 and 2016, survival rates of patients with oral cancer in stages I to IV were: 79.9%, 71.0%, 56.5% and 35.6%, respectively. If detected early, the survival rate will be improved.

At present, oral mucosal screening is an important method for clinical evaluation of oral cancer, and results of tissue biopsy at the lesion are used as the basis for diagnosis. However, at present, the oral mucosal screening needs to be performed by professional oral health personnel (e.g., dentists, oral health hygienists, dental therapists, oral health therapists, etc.), and in many areas, the diagnosis of oral cancer is delayed due to lack of professional oral health personnel. Therefore, if it is possible to analyze whether there is a tumor marker (biomarker) in the sample, an early diagnosis rate of oral cancer can be improved.

Currently, there is no tumor marker for routine identification of oral cancer. According to a report in the Proceedings of the National Academy of Sciences of the United States of America (PNAS) in 2016, matrix metalloproteinase-1 (MMP-1) was quantified by mass spectrometry quantitative analysis, which showed that a difference in MMP-1 expression between saliva samples of patients and saliva samples of controls was as high as 83-fold (the differences in other molecules were −1.3-fold to 5.5-fold), so MMP-1 is the most potential molecule as the tumor marker for oral cancer.

Since the existing mass spectrometry quantitative analysis method for MMP-1 is not suitable for routine quantitative analysis of a large number of samples, it is hoped to develop a detection kit for MMP-1 for screening of oral cancer.

SUMMARY

Some embodiments of the present disclosure provides a monoclonal antibody, which includes a heavy chain variable region sequence and a light chain variable region sequence. The heavy chain variable region sequence includes i) a CDR1 selected from the group consisting of SEQ ID NOs: 1, 7 and 13, ii) a CDR2 selected from the group consisting of SEQ ID NOs: 2, 8 and 14, and iii) a CDR3 selected from the group consisting of SEQ ID NOs: 3, 9 and 15. The light chain variable region sequence includes i) a CDR1 selected from the group consisting of SEQ ID NOs: 4, 10 and 16, ii) a CDR2 selected from the group consisting of SEQ ID NOs: 5, 11 and 17, and iii) a CDR3 selected from the group consisting of SEQ ID NOs: 6, 12 and 18.

In some embodiments, the heavy chain variable region sequence includes amino acid sequences of SEQ ID NOs: 1, 2, and 3, and the light chain variable region sequence includes amino acid sequences of SEQ ID NOs: 4, 5, and 6.

In some embodiments, the heavy chain variable region sequence includes amino acid sequences of SEQ ID NOs: 7, 8, and 9, and the light chain variable region sequence includes amino acid sequences of SEQ ID NOs: 10, 11, and 12.

In some embodiments, the heavy chain variable region sequence includes amino acid sequences of SEQ ID NOs: 13, 14 and 15, and the light chain variable region sequence includes amino acid sequences of SEQ ID NOs: 16, 17, and 18.

Some embodiments of the present disclosure provides a polynucleotide, which encodes the above-mentioned amino acid sequences or has a sequence complementary to a nucleotide sequence that encodes the above-mentioned monoclonal antibody.

Some embodiments of the present disclosure provides a detection kit, and the detection kit includes a monoclonal antibody A, in which the monoclonal antibody A includes a heavy chain variable region and a light chain variable region. The heavy chain variable region includes amino acid sequences of SEQ ID NOs: 1, 2, and 3. The light chain variable region includes amino acid sequences of SEQ ID NOs: 4, 5, and 6.

In some embodiments, the detection kit further includes an enzyme immunoassay reagent kit, a colloidal gold immunoassay test strip or a combination thereof.

In some embodiments, the enzyme immunoassay reagent kit includes: a monoclonal antibody B. The monoclonal antibody B includes a heavy chain variable region and a light chain variable region. The heavy chain variable region includes amino acid sequences of SEQ ID NOs: 7, 8, and 9. The light chain variable region includes amino acid sequences of SEQ ID NOs: 10, 11, and 12.

In some embodiments, the monoclonal antibody B is linked to a chromogenic group.

In some embodiments, the colloidal gold immunoassay test strip includes a monoclonal antibody C. The monoclonal antibody C includes a heavy chain variable region and a light chain variable region. The heavy chain variable region includes amino acid sequences of SEQ ID NOs: 13, 14, and 15. The light chain variable region includes amino acid sequences of SEQ ID NOs: 16, 17, and 18.

In some embodiments, the colloidal gold immunoassay test strip further includes the monoclonal antibody A, and the monoclonal antibody A in the colloidal gold immunoassay test strip is linked to a gold particle.

Some embodiments of the present disclosure provides a method for detecting matrix metalloproteinase-1 in vitro, which includes detecting matrix metalloproteinase-1 in a sample using the above-mentioned detection kit.

In some embodiments, the sample includes a body fluid or a blood.

In some embodiments, the body fluid includes an oral secretion or a respiratory secretion.

BRIEF DESCRIPTION OF THE DRAWINGS

In order to make the above-mentioned and other objects, features, advantages and embodiments of the present disclosure more clearly understood, descriptions of accompanying drawings are as follows.

DETAILED DESCRIPTION

Figure 1A:
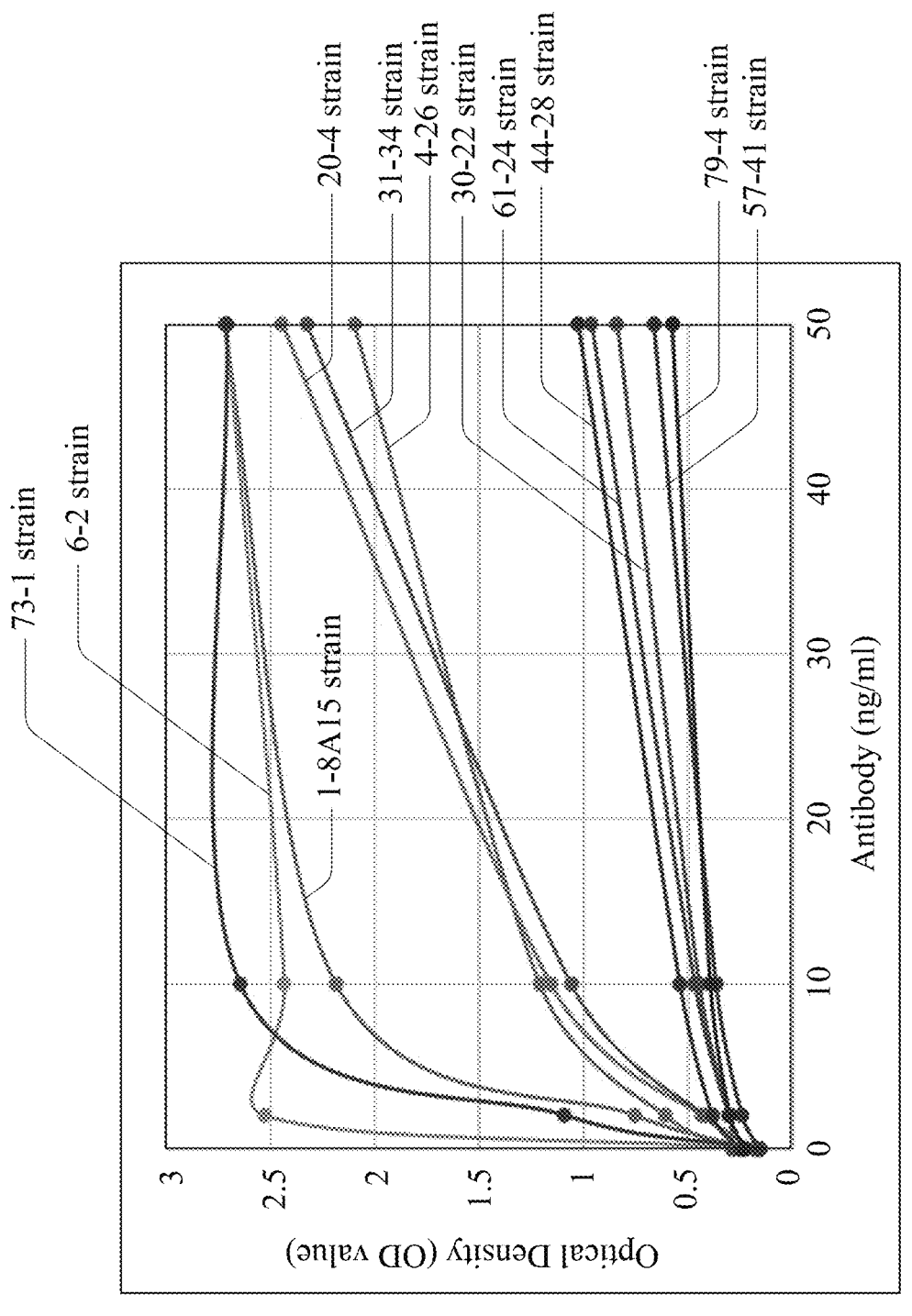
FIGS. 1A and 1B illustrate comparative graphs of testing binding abilities of self-produced monoclonal antibodies to MMP-1 using an enzyme immunoassay in one embodiment of the present disclosure.

In order that the present disclosure is described in detail and completeness, implementation aspects and specific embodiments of the present disclosure with illustrative description are presented, but those are not the only form for implementation or use of the specific embodiments of the present disclosure. The embodiments disclosed herein may be combined or substituted with each other in an advantageous manner, and other embodiments may be added to an embodiment without further description. In the following description, numerous specific details will be described in detail in order to enable the reader to fully understand the following embodiments. However, the embodiments of the present disclosure may be practiced without these specific details.

In this description, unless the context specifically dictates otherwise, "a" and "the" may mean a single or a plurality. It will be further understood that "comprise", "include", "have", and similar terms as used herein indicate described features, regions, integers, steps, operations, elements and/or components, but not exclude other features, regions, integers, steps, operations, elements, components and/or groups.

Although a series of operations or steps are described below to illustrate the method disclosed herein, the order of the operations or steps is not to be construed as limiting. For example, certain operations or steps may be performed in a different order and/or concurrently with other steps. In addition, not all illustrated operations, steps, and/or features are required to implement embodiments of the present disclosure. Moreover, each of the operations or steps described herein can include a plurality of sub-steps or actions.

In this description, a "CDR" (complementarity determining region), is a region where an antigen is in contact with an antibody, and is a portion of a variable region of the antibody. Generally, there are three CDRs in the variable region of the antibody, which are a CDR1, a CDR2, and a CDR3.

In this description, a "derived sequence" refers to a sequence modified at a 3' end or a 5' end of a nucleotide sequence.

In some embodiments of the present disclosure, a monoclonal antibody that recognizes matrix metalloproteinase-1 (MMP-1) is provided, which includes a heavy chain variable region sequence and a light chain variable region sequence. The heavy chain variable region sequence includes i) a CDR1 selected from the group consisting of SEQ ID NOs: 1, 7 and 13, ii) a CDR2 selected from the group consisting of SEQ ID NOs: 2, 8 and 14, and iii) a CDR3 selected from the group consisting of SEQ ID NOs: 3, 9 and 15. The light chain variable region sequence includes i) a CDR1 of an amino acid sequence selected from the group consisting of SEQ ID NOs: 4, 10 and 16, ii) a CDR2 selected from the group consisting of SEQ ID NOs: 5, 11 and 17, and iii) a CDR3 selected from the group consisting of SEQ ID NOs: 6, 12 and 18.

In some embodiments, the heavy chain variable region sequence includes amino acid sequences of SEQ ID NOs: 1, 2, and 3, and the light chain variable region sequence includes amino acid sequences of SEQ ID NOs: 4, 5, and 6. In some embodiments, the heavy chain variable region sequence includes amino acid sequences of SEQ ID NOs: 7, 8, and 9, and the light chain variable region sequence includes amino acid sequences of SEQ ID NOs: 10, 11, and 12. In some embodiments, the heavy chain variable region sequence includes amino acid sequences of SEQ ID NOs: 13, 14, and 15, and the light chain variable region sequence includes amino acid sequences of SEQ ID NOs: 16, 17, and 18.

In some embodiments of the present disclosure, a polynucleotide is provided, which encodes the aforementioned amino acid sequences, or has a sequence complementary to the aforementioned polynucleotide sequence. In one embodiment, the polynucleotide may further include a derivative sequence.

In some embodiments of the present disclosure, a detection kit is provided, in which the detection kit may be used to detect a clinical sample, such as a body fluid (e.g., an oral secretion or a respiratory secretion) or a blood. The detection kit includes a monoclonal antibody A. A heavy chain variable region of the monoclonal antibody A includes amino acid sequences of SEQ ID NOs: 1, 2, and 3; a light chain variable region of the monoclonal antibody A includes amino acid sequences of SEQ ID NOs: 4, 5, and 6. In some embodiments, a heavy chain variable region of the monoclonal antibody A includes amino acid sequences of a CDR1, which is SEQ ID NO: 1, and a CDR2, which is SEQ ID NO: 2, and a CDR3, which is SEQ ID NO: 3; a light chain variable region of the monoclonal antibody A includes amino acid sequences a CDR1, which is SEQ ID NO: 4, and a CDR2, which is SEQ ID NO: 5, and a CDR3, which is SEQ ID NO: 6.

In some embodiments, the detection kit includes an enzyme immunoassay reagent kit, a colloidal gold immunoassay test strip or a combination thereof.

In some embodiments, the enzyme immunoassay reagent kit uses a sandwich enzyme-linked immunosorbent assay (sandwich ELISA) with the monoclonal antibody A as a capture antibody. In one embodiment, the enzyme immunoassay reagent kit includes the monoclonal antibody A and a monoclonal antibody B, in which the monoclonal antibody A is acted as a capture antibody, and the monoclonal antibody B is linked to a chromogenic group and is acted as a detection antibody. A heavy chain variable region of the monoclonal antibody B includes amino acid sequences of SEQ ID NOs: 7, 8, and 9, and a light chain variable region of the monoclonal antibody B includes amino acid sequences of SEQ ID NOs: 10, 11, and 12. In one embodiment, a heavy chain variable region of the monoclonal antibody B includes amino acid sequences of a CDR1, which is SEQ ID NO: 7, and a CDR2, which is SEQ ID NO: 8, and a CDR3, which is SEQ ID NO: 9; a light chain variable region of the monoclonal antibody B includes amino acid sequences of a CDR1, which is SEQ ID NO: 10, and a CDR2, which is SEQ ID NO: 11, and a CDR3, which is SEQ ID NO: 12. In one embodiment, the chromogenic group includes a fluorescent group or a chemiluminescent group (e.g., horseradish peroxidase (HRP)).

It is worth noting that in some embodiments of the present disclosure, it is disclosed to use human recombinant MMP-1 (full-length MMP-1) as immunogen to self-produce 11 monoclonal antibodies and to screen out monoclonal antibody pairs (capture antibody: the monoclonal antibody A; and detection antibody: the monoclonal antibody B) that can be used in the enzyme immunoassay reagent kit, which overcome limitations derived from the monoclonal antibody linked to the chromogenic group, such as significantly reduced ability to bind MMP-1, high background values that often occur in detection of clinical samples, and insufficient sensitivity, and have better sensitivity compared with other pairs (some cannot even detect MMP-1). Furthermore, it should be emphasized that such pairs are not correlated with ability of the monoclonal antibody to bind MMP-1. It is worth mentioning that the monoclonal antibody pairs of some embodiments of the present disclosure have higher sensitivity compared with other antibody pairs, such as a commercially available antibody (immunogen is the $20^{th}$ to $469^{th}$ amino acids of MMP-1) used as a capture antibody, other monoclonal antibodies produced using protease-inactive MMP-1 as immunogen, or polyclonal antibodies produced using a MMP-1 fragment (e.g., any fragment from the $100^{th}$ to $300^{th}$ amino acids of MMP-1, or a protease-inactive fragment) as immunogen.

In some embodiments, the colloidal gold immunoassay test strip includes a colloidal gold pad and an assay plate overlapped with each other, and the colloidal gold pad is sprayed with a colloidal gold pad solution including a detection antibody-gold particle conjugate, and a surface of the assay plate has a nitrocellulose membrane, and a solution containing a capture antibody is applied thereon as a measurement line. In one embodiment, the colloidal gold immunoassay test strip includes the monoclonal antibody A and a monoclonal antibody C, and the monoclonal antibody A is used as a detection antibody linked to a gold particle, and the monoclonal antibody C is used as a capture antibody. A heavy chain variable region of the monoclonal antibody C includes amino acid sequences of SEQ ID NOs: 13, 14, and 15, and a light chain variable region of the monoclonal antibody C includes amino acid sequences of SEQ ID NOs: 16, 17, and 18. In some embodiments, a heavy chain variable region of the monoclonal antibody C includes amino acid sequences of a CDR1, which is SEQ ID NO: 13, and a CDR2, which is SEQ ID NO: 14, and a CDR3, which is SEQ ID NO: 15; a light chain variable region includes amino acid sequences of a CDR1, which is SEQ ID NO: 16, and a CDR2 of which is SEQ ID NO: 17, and a CDR3, which is SEQ ID NO: 18.

It is worth noting that, in some embodiments of the present disclosure, monoclonal antibody pairs that can be used in the colloidal gold immunoassay test strip (capture antibody: the monoclonal antibody C; and detection antibody: the monoclonal antibody A) are screened out from the monoclonal antibody pairs that can be used in the enzyme immunoassay reagent kit, and the detection antibody is successfully linked to the gold particle and overcomes an issue that some monoclonal antibodies cannot be linked to the gold particle, and some combinations have better sensitivity compared with other combinations. In addition, it was also revealed that the pair with the best sensitivity in the enzyme immunoassay reagent kit may not have the best sensitivity in the colloidal gold immunoassay test strip. That is, if the antibody pair in one detection system is to be applied to another detection system, pros and cons of sensitivity still need to be verified by actual tests, and it is not necessarily positively correlated with the existing known detection system.

In some embodiments of the present disclosure, a method for detecting MMP-1 is provided, which includes detecting MMP-1 in a sample using the aforementioned detection kit. For example, detecting presence/absence or a content of MMP-1 can be determined by presence/absence of coloration or a quantified reading value of coloration (e.g., optical density value (OD value)) of the enzyme immunoassay reagent kit, the colloidal gold immunoassay test strip, or a combination thereof. In some embodiments, the sample includes a body fluid (e.g., an oral secretion ora respiratory secretion) ora blood. In one embodiment, the detection kit can use the enzyme immunoassay reagent kit for quantification, and use the colloidal gold immunoassay test strip for rapid screening, so that both qualitative and quantitative results can be obtained at the same time.

Since MMP-1 can be used as a detection index of oral cancer, the detection kit and the detection method of MMP-1 provided by some embodiments of the present disclosure can be simultaneously used for oral cancer screening. Such application does not need to be performed by professional oral health care personnel, which can increase popularity of screening and accelerate diagnosis of oral cancer patients and improve probability of cure.

In order to further illustrate the monoclonal antibody, polynucleotide, detection kit, and detection method of MMP-1 provided by various embodiments of the present disclosure, following implementations were carried out. It should be noted that the following embodiments are provided for exemplary purposes only, and are not intended to limit the present disclosure.

Embodiment 1. Development Process of Monoclonal Antibody

First, human MMP-1 recombinant protein that retained protease activity was used as immunogen, and mouse MMP-1 monoclonal antibody cell strains were developed through immune response of the mouse, and 11 mouse monoclonal antibody cell strains were screened out, and a cell fluid was collected and purified to obtain each monoclonal antibody, and named as: 1-8A12 strain, 4-26 strain, 6-2 strain, 20-4 strain, 30-22 strain, 31-34 strain, 44-28 strain, 57-41 strain, 61-24 strain, 73-1 strain and 79-4 strain.

Embodiment 2-1. Enzyme Immunoassay Reagent Kit for Detecting MMP-1-Test of Ability of Each monoclonal antibody to bind MMP-1

In order to test whether each monoclonal antibody was able to specifically bind MMP-1, after serial dilution of the aforementioned 11 monoclonal antibody strains, binding of the monoclonal antibodies to human recombinant MMP-1 was tested using direct ELISA, and results are shown in FIG. 1A.

FIG. 1A showed that each monoclonal antibody was able to specifically bind MMP-1, and the monoclonal antibodies had different binding abilities to MMP-1, and an order of the binding abilities from strong to weak was: 6-2 strain>73-1 strain>1-8A12 strain>4-26 strain>20-4 strain>31-34 strain>44-28 strain>61-24 strain>30-22 strain>57-41 strain>79-7 strain.

In addition, in order to test whether the monoclonal antibody could be used as the detection antibody in the

8 detection antibody (linked to HRP) of the enzyme immunoassay reagent kit, and paired tests were carried out. Pairs of 11×10=110 combinations would theoretically be generated, however, 3 monoclonal antibody strains were excluded because those were extremely ineffective in the paired tests. In fact, the paired tests of a total of 92 combinations were completed, and optimally pairs that could detect MMP-1 were screened out.

A test process of each pair, taking 1-8A12 strain as an example, is described as follows: (1) Sandwich ELISA with 1-8A12 strain as the capture antibody and 4-26-HRP as the detection antibody was performed. The capture antibody had 4 concentrations, and the detection antibody had 6 concentrations. A set of the pair was to test 24 conditions. A difference in OD values (sample value-background value) between a solution containing human recombinant MMP-1 (sample value) and a solution without human recombinant MMP-1 (background value) was calculated under these 24 conditions. The higher the value, the better the binding ability of the antibody pair to detectable MMP-1. (2) The paired tests of 92 combinations were completed according to the aforementioned step 1, and results are listed in Table 1 below. The value in the table 1 is a maximum value of the differences in the OD values of each pair in the paired tests.

TABLE 1

Table of maximum difference from sample value minus background value of each pair

| Capture antibody | Detection antibody | | | | | | | | | | |
|---|---|---|---|---|---|---|---|---|---|---|---|
| | 1-8A12-HRP | 4-26-HRP | 6-2-HRP | 20-4-HRP | 30-22-HRP | 31-34-HRP | 44-28-HRP | 57-41-HRP | 61-24-HRP | 73-1-HRP | 79-4-HRP |
| 1-8A12 | | 2.674 | 2.572 | 1.547 | 2.203 | 2.387 | 2.607 | 1.011 | 1.219 | — | 0.857 |
| 4-26 | 2.413 | | 0.587 | — | — | 2.342 | — | — | — | 2.48 | — |
| 6-2 | 2.211 | 0.600 | | 2.450 | — | 2.565 | 0.511 | 1.466 | 1.947 | 2.327 | NA |
| 20-4 | — | NA | 0.792 | | NA | 0.632 | NA | — | NA | 0.514 | NA |
| 30-22 | 1.543 | — | — | — | | — | — | — | 0.786 | 0.725 | 0.545 |
| 31-34 | 2.798 | 1.920 | 2.505 | 2.702 | 0.882 | | 0.772 | 2.705 | 0.689 | 2.677 | NA |
| 44-28 | 2.663 | — | — | 1.173 | — | 0.836 | | — | 0.792 | 1.375 | — |
| 57-41 | — | NA | 0.931 | — | NA | 1.643 | NA | | NA | 0.85 | NA |
| 61-24 | — | — | 0.503 | — | 1.268 | 0.892 | 0.863 | — | | 0.862 | — |
| 73-1 | — | 2.645 | 2.785 | 1.938 | 2.613 | 2.743 | 2.512 | 2.179 | 1.406 | | NA |
| 79-4 | — | — | NA | NA | — | NA | — | NA | — | NA | |

Figure 1B:
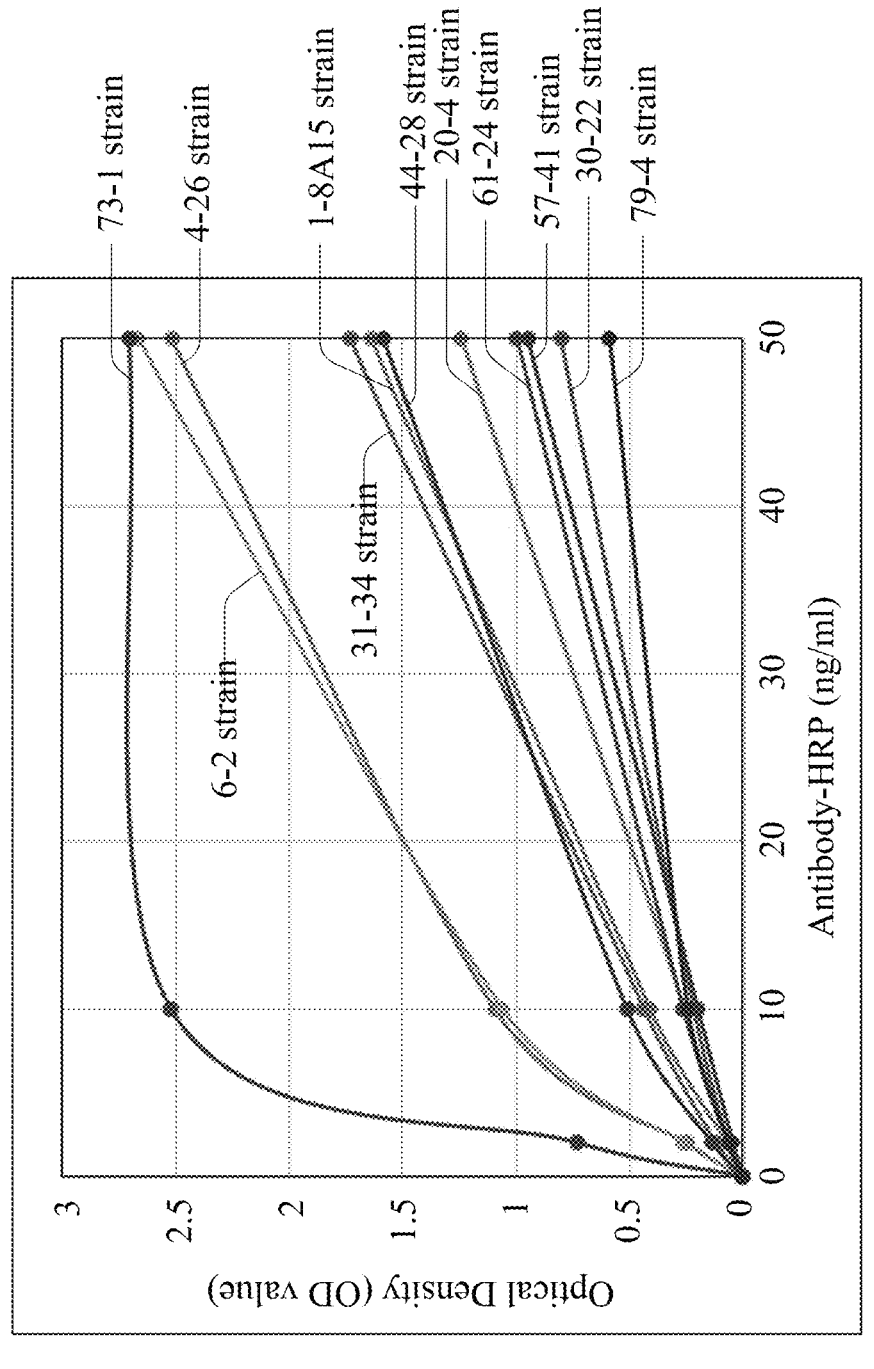

Note:
The differences <0.5 are marked with "—", and those not tested are marked with "NA".

enzyme immunoassay, that is, whether the monoclonal antibody still had binding ability of MMP-1 after being linked to a chromogenic group, after each monoclonal antibody was linked to HRP, a binding ability test of MMP-1 was carried out in the same way as in the aforementioned FIG. 1A, and results are shown in FIG. 1B.

FIG. 1B showed that each monoclonal antibody after being linked to HRP still had ability to specifically bind human recombinant MMP-1. However, relative to FIG. 1A, the monoclonal antibodies linked to HRP showed a slight change in binding abilities to human recombinant MMP-1, and an order from strong to weak was: 73-1-HRP>4-26-HRP=6-2-HRP>44-28-HRP>31-34-HRP>1-8A12-HRP>20-4-HRP>61-24-HRP>57-41-HRP>30-22-HRP>79-7-HRP.

Embodiment 2-2. Enzyme Immunoassay Reagent Kit for Detecting MMP-1-Screening of Antibody Pairs The above-mentioned 11 monoclonal antibody strains were respectively used as the capture antibody and the Table 1 showed that the monoclonal antibody pairs with stronger signal (higher difference) in the paired tests had no absolute relationship with the binding ability of MMP-1 of the individual monoclonal antibody. That is, the optimal antibody pairs suitable for the enzyme immunoassay reagent kit could not be determined by the binding ability of MMP-1 of the individual monoclonal antibody, and should be screened out by the actual paired tests.

Embodiment 2-3. Enzyme Immunoassay Reagent Kit for Detecting MMP-1-Standard Concentration Curve of Each Antibody Pair According to the results of Embodiment 2-2, sandwich ELISA was performed on 12 antibody pairs (listed in Table 2) to obtain a range of human recombinant MMP-1 standard concentration curve detectable by each antibody pair, and results are listed in Table 3.

TABLE 2

| | | | | | | Comparison table of each antibody pair | | | | | | |
|---|---|---|---|---|---|---|---|---|---|---|---|---|
| | | | | | | No. | | | | | | |
| | No. 1 | No. 2 | No. 3 | No. 4 | No. 5 | No. 6 | No. 7 | No. 8 | No. 9 | No. 10 | No. 11 | No. 12 |
| Capture antibody | 1-8A12 | 1-8A12 | 31-34 | 31-34 | 73-1 | 73-1 | 6-2 | 6-2 | 6-2 | 6-2 | 31-34 | 31-34 |
| Detection antibody (HRP) | 31-34 | 6-2 | 1-8A12 | 73-1 | 6-2 | 31-34 | 1-8A12 | 31-34 | 73-1 | 20-4 | 20-4 | 57-41 |

TABLE 3

Comparison table of ranges of standard concentration curves of antibody paired tests

| | | OD value Concentration (ng/ml) | | | | |
|---|---|---|---|---|---|---|
| | | 0.01 | 0.039 | 0.156 | 0.625 | 2.5 |
| Pairing number | No. 1 | −0.005 | 0.004* | 0.063* | 0.266* | 1.042* |
| | No. 2 | 0* | 0.026* | 0.131* | 0.598* | 2.332* |
| | No. 3 | −0.003* | 0.016* | 0.1* | 0.46* | 1.911* |
| | No. 4 | 0.013 | 0.053* | 0.205* | 0.846* | 2.506* |
| | No. 5 | 0.013 | 0.065* | 0.274* | 1.124* | 2.639* |
| | No. 6 | −0.047* | −0.023* | 0.128* | 0.766* | 2.43* |
| | No. 7 | −0.007 | −0.001* | 0.017* | 0.114* | 0.604* |
| | No. 8 | −0.009 | −0.006* | 0.008* | 0.08* | 0.614* |
| | No. 9 | −0.003* | 0.022* | 0.113* | 0.507* | 1.868* |
| | No. 10 | 0.003* | 0.011* | 0.045* | 0.194* | 0.783* |
| | No. 11 | −0.001* | 0.01* | 0.062* | 0.296* | 1.311* |
| | No. 12 | −0.008* | 0.002* | 0.051* | 0.247* | 1.109* |

The results in Table 3 showed that the OD values of each pair increased with increasing MMP-1 concentration when a tested concentration range of human recombinant MMP-1 was between 0.01 and 2.5 ng/ml.

Next, recovery was used to evaluate a concentration range of the standard curve detectable by each antibody pair, and recovery 80-120 was set as a trustworthy range, and concentrations falling within the trustworthy range are marked with an asterisk (*). Results showed that the concentration ranges of the standard curves of the 12 antibody pairs were different, and some pairs had negative values at low concentrations, which indicated that the background value was high, which was not conducive to detection of low-concentration samples.

Embodiment 2-4. Enzyme Immunoassay Reagent Kit for Detecting MMP-1-Detecting Endogenous MMP-1 in Clinical Saliva Samples Next, 8 clinical saliva samples with known endogenous MMP-1 contents (the content was analyzed by multiplex LC-MRM-MS) were detected with using the 12 antibody pairs of Embodiment 2-3 to confirm whether the antibody pairs could detect endogenous MMP-1 in the clinical saliva samples in addition to human recombinant MMP-1, and results are shown in Table 4.

TABLE 4

Comparison table of OD values for detection of endogenous MMP-1 in saliva samples by antibody pairs

| | | OD value Sample number | | | | | | | |
|---|---|---|---|---|---|---|---|---|---|
| | | 1 | 2 | 3 | 4 | 5 | 6 | 7 | 8 |
| | | concentration (pg/ml) | | | | | | | |
| | | 14821.9 | 5041.1 | 1503.2 | 6.4 | 285.6 | 27.1 | 120.6 | 0 |
| Pairing number | No. 1 | 2.895 | 1.041 | 0.868 | 0 | 0.164 | 0.116 | 0.08 | −0.015 |
| | No. 2 | 2.899 | 2.682 | 0.868 | 0.007 | 0.266 | 0.059 | 0.145 | 0.013 |
| | No. 3 | 2.867 | 2.559 | 0.663 | −0.003 | 0.223 | 0.039 | 0.081 | 0 |
| | No. 4 | 3.011 | 2.66 | 0.981 | 0.015 | 0.296 | 0.062 | 0.152 | 0.025 |
| | No. 5 | 2.878 | 2.769 | 1.55 | 0.015 | 0.538 | 0.126 | 0.285 | 0.017 |
| | No. 6 | 2.941 | 2.825 | 1.333 | −0.051 | 0.39 | 0.034 | 0.144 | −0.055 |
| | No. 7 | 2.926 | 2.163 | 0.273 | −0.004 | 0.086 | 0.011 | 0.031 | −0.003 |
| | No. 8 | 2.94 | 2.643 | 0.173 | −0.009 | 0.025 | 0.007 | 0.006 | −0.004 |
| | No. 9 | 2.926 | 2.716 | 0.906 | 0.005 | 0.239 | 0.048 | 0.145 | 0.001 |
| | No. 10 | 2.994 | 2.05 | 0.326 | 0.006 | 0.081 | 0.029 | 0.053 | 0.009 |
| | No. 11 | 2.938 | 2.209 | 0.363 | −0.002 | 0.097 | 0.025 | 0.047 | 0.004 |
| | No. 12 | 2.951 | 1.756 | 0.292 | −0.008 | 0.069 | 0.035 | 0.042 | 0.019 |

The results showed that all of the 12 antibody pairs could detect endogenous MMP-1 in the saliva samples, and MMP-1 contents detected by most of the pairs were consistent with actual contents, which showed that the 12 antibody pairs also had sufficient specificity to detect MMP-1 in the saliva samples. According to the results in Table 4, No. 2, No. 4, No. 5, and No. 10 with better sensitivities were selected for further evaluation.

Figure 2A:
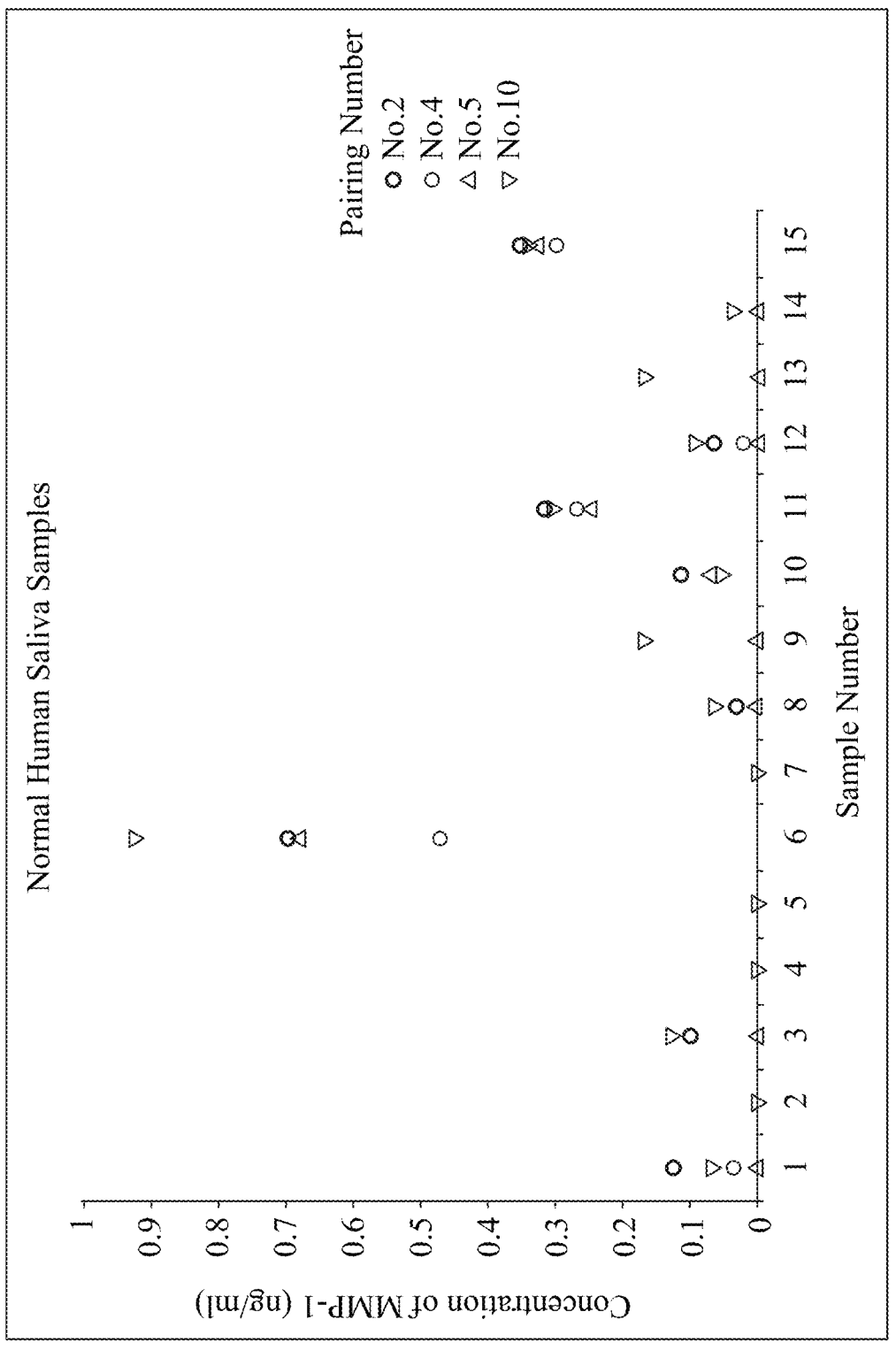
FIGS. 2A and 2B illustrate concentration profiles measured by an enzyme immunoassay in saliva samples of normal human (FIG. 2A) and patients with oral cancer (FIG. 2B) in one embodiment of the present disclosure, in which monoclonal antibodies of four optimally pairs were used as a capture antibody and a detection antibody of the enzyme immunoassay, respectively.
Figure 2B:
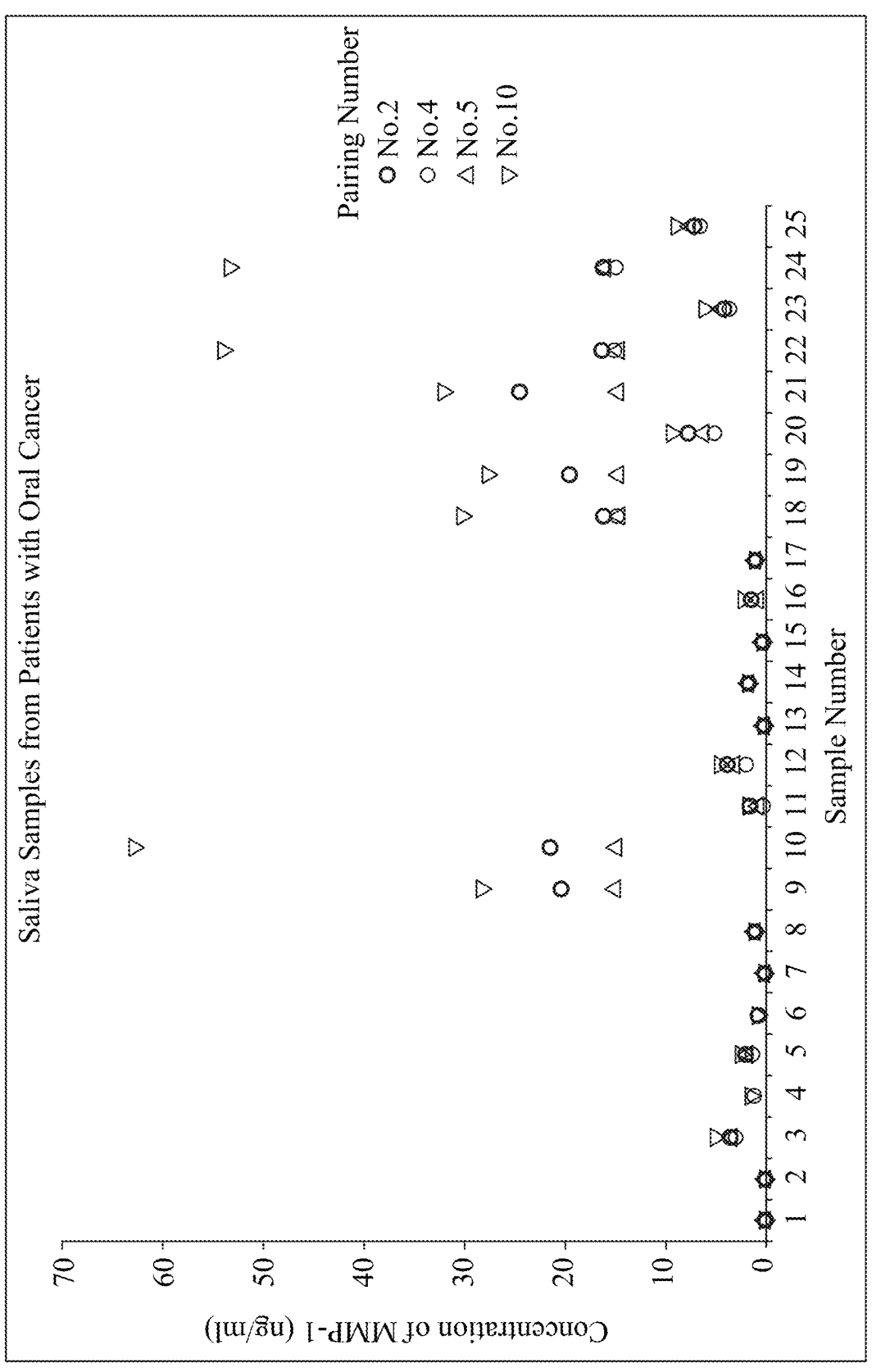

In order to evaluate feasibility of clinical application, 15 clinical saliva samples from normal healthy people (healthy control, HC) and 25 clinical saliva samples from patients with oral cancer (oral squamous cell carcinoma, OSCC) were collected and then diluted 5 times for enzyme immunoassay experiments. Results are shown in FIG. 2A (a group of normal human) and FIG. 2B (a group of patients with oral cancer). Further data analysis was performed with FIG. 2A and FIG. 2B.

The results showed that measured values of 4 antibody pairs were significantly correlated (Spearman's rho=0.953-0.988) in both the group of normal human and the group of patients with oral cancer; in addition, a receiver operating characteristic curve (ROC) analysis showed that the 4 antibody pairs were suitable for detecting endogenous MMP-1 (area under the curve of ROC (AUC of ROC)=0.937-0.967), and sensitivities and specificities of the 4 pairs obtained by the ROC analysis are summarized in Table 5.

TABLE 5

Sensitivity and specificity analysis of antibody pairs

| Pairing number | Sensitivity | Specificity |
|---|---|---|
| No. 2 | 80.00% | 100.00% |
| No. 4 | 94.40% | 80.00% |
| No. 5 | 76.20% | 100.00% |
| No. 10 | 88.00% | 93.30% |

According to Table 5, the antibody pair with higher sensitivity, No. 4, was selected for preparation of MMP-1 enzyme immunoassay reagent kit.

Embodiment 2-5. Enzyme Immunoassay Reagent Kit for Detecting MMP-1-Functional Test According to Global Laboratory Standards for a Healthier World published by the American Association for Clinical and Laboratory Standardization, a functional test was performed on a MMP-1 enzyme immunoassay reagent kit using the No. 4 antibody pair, and results were as follows.
1. Sensitivity analysis (refer to standard Ep17-A2), limit of blank (LoB) was 57.40 pg/ml, and limit of detection (LoD) was 117.02 pg/ml.
2. Linear analysis (refer to standard Ep06-A), the best nonlinear polynomial was a 3-level regression, and a concentration was linearly distributed between 140 and 8,000 pg/ml (non-linearity≤5%).
3. Precision analysis (refer to standard Ep05-A3), average CV (%) of repeatability was 4.809%, and average CV (%) of within-laboratory precision was 9.569%.

Embodiment 3-1. Colloidal Gold Immunoassay Test Strip for Detecting MMP-1-Selection of Combinations of Antibody Matching Next, the self-produced monoclonal antibodies were further tested to find antibody combinations suitable for a colloidal gold immunoassay test trip for detection of MMP-1. Please refer to FIG. 3A, a schematic diagram of the colloidal gold immunoassay test strip 1 including a colloidal gold pad 110 and an assay plate 120, which could be stacked on each other, for example, the colloidal gold pad 110 was stacked on the assay plate 120 or the assay plate 120 was stacked on the colloidal gold pad 110, and a colloidal gold pad solution 111 containing a detection antibody-gold particle conjugate was sprayed on the colloidal gold pad 110, and a surface of the assay plate 120 was covered with a nitrocellulose membrane, and an measurement line 122 was formed by coating a solution containing a capture antibody on the nitrocellulose membrane. In addition, a solution containing an internal control antibody was added on the nitrocellulose membrane, which could be acted as an internal control line 121. During the test, a sample was added to the colloidal gold pad 110 containing the detection antibody-gold particle conjugate, and the sample moved from the colloidal gold pad 110 to the nitrocellulose membrane on the assay plate 120 through immunochromatography. If MMP-1 had been bound to the detection antibody-gold particle conjugate, the capture antibody on the measurement line 122 would capture MMP-1 bound to the detection antibody-gold particle conjugate and then aggregate to form an orange to red signal (a color of the gold particle). Therefore, a test result could be judged by whether the measurement line 122 is colored or not.

In order to select combinations of antibody matching, the monoclonal antibodies, 1-8A12 strain, 6-2 strain, 20-4 strain, 31-34 strain and 73-1 strain, which were used in the 4 antibody pairs (No. 2, No. 4, No. 5, No. 10) with better sensitivities in Embodiment 2-4, were paired and tested as follows.

First, the five antibodies were reacted with nano-scale gold particles (diameter<100 nm) to form a "detection antibody-gold particle conjugate." However, because 1-8A12 strain and 73-1 strain did not react well with the gold particles, the gold particles could not be linked to the detection antibody. Therefore, only 6-2-gold particle, 20-4-gold particle and 31-34-gold particle were paired with human recombinant MMP-1, and there were a total of 10 combinations. Results are shown in Table 6.

TABLE 6

Detection limit of antibody pair combination for colloidal gold immunoassay test strip

| Detection antibody (colloidal gold pad) | Capture antibody (measurement line) | | | | |
|---|---|---|---|---|---|
| | 1-8A12 | 6-2 | 20-4 | 31-34 | 73-1 |
| 6-2-gold particle | Combination A 100 ng/ml | | Combination F less than 100 ng/ml | Combination H less than 100 ng/ml | No signal |

TABLE 6-continued

Detection limit of antibody pair combination for colloidal gold immunoassay test strip

| Detection antibody (colloidal | Capture antibody (measurement line) | | | | |
|---|---|---|---|---|---|
| gold pad) | 1-8A12 | 6-2 | 20-4 | 31-34 | 73-1 |
| 20-4-gold particle | Combination B 100 ng/ml | Combination D 100 ng/ml | | Combination I 100 ng/ml | No signal |
| 31-34-gold particle | Combination C 0.5 ng/ml | Combination E less than 100 ng/ml | Combination G less than 100 ng/ml | | Combination J 10 ng/ml |

According to Table 6, since the combination C could achieve better sensitivity, therefore, the combination C was selected for subsequent clinical sample testing.

Embodiment 3-2. Colloidal Gold Immunoassay Test Strip for Detecting MMP-1-Testing of Clinical Samples To evaluate feasibility of detecting clinical samples with the colloidal gold immunoassay test strip containing the combination C, 215 saliva samples were tested and cross-compared by enzyme immunoassay.

Figure 3B:
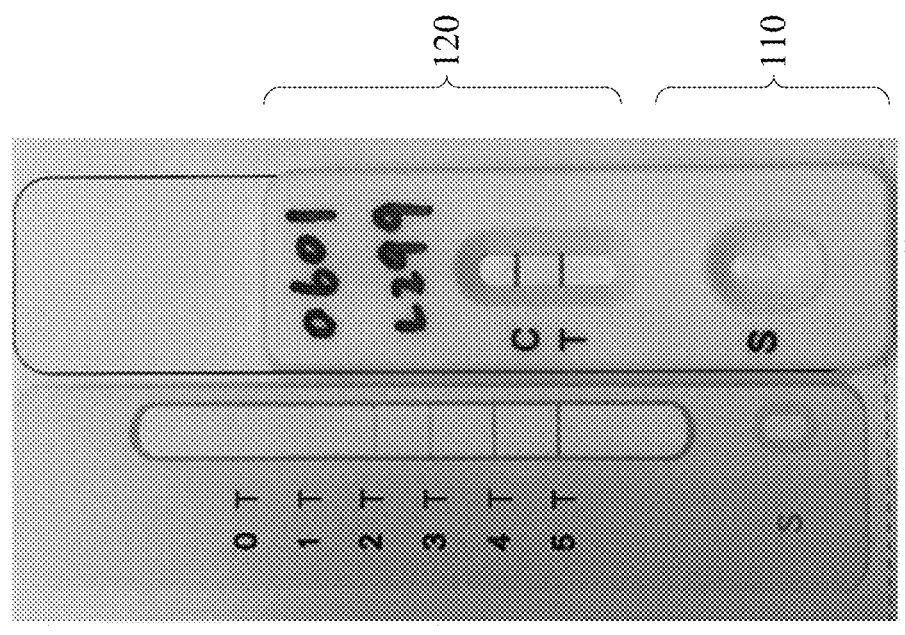
FIG. 3B illustrates a schematic diagram of a colorimetric card presenting grades obtained by a colloidal gold immunoassay test strip in one embodiment of the present disclosure.
Figure 3A:
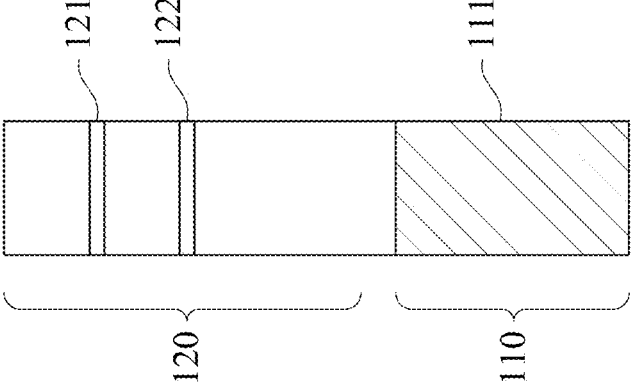
FIG. 3A illustrates a schematic diagram of a colloidal gold immunoassay test strip in one embodiment of the present disclosure.

For the colloidal gold immunoassay test strip, please refer to FIG. 3B. Reaction degrees of the samples were scored against a colorimetric card. The colorimetric card was divided into 0 to 5 points according to color intensities of the measurement line 122. The colorimetric card was used to score 0, 0-1 (0.5), 1, 1-2 (1.5), 2, 2-3 (2.5), 3, 3-4 (3.5), 4, 4-5 (4.5), 5, >5 (5.5), a total of 12 grades. Next, an X-Y distribution diagram of the grades of the colorimetric card and the concentration of MMP-1 measured by the enzyme immunoassay method was made, and results are shown in FIG. 4.

Figure 4:
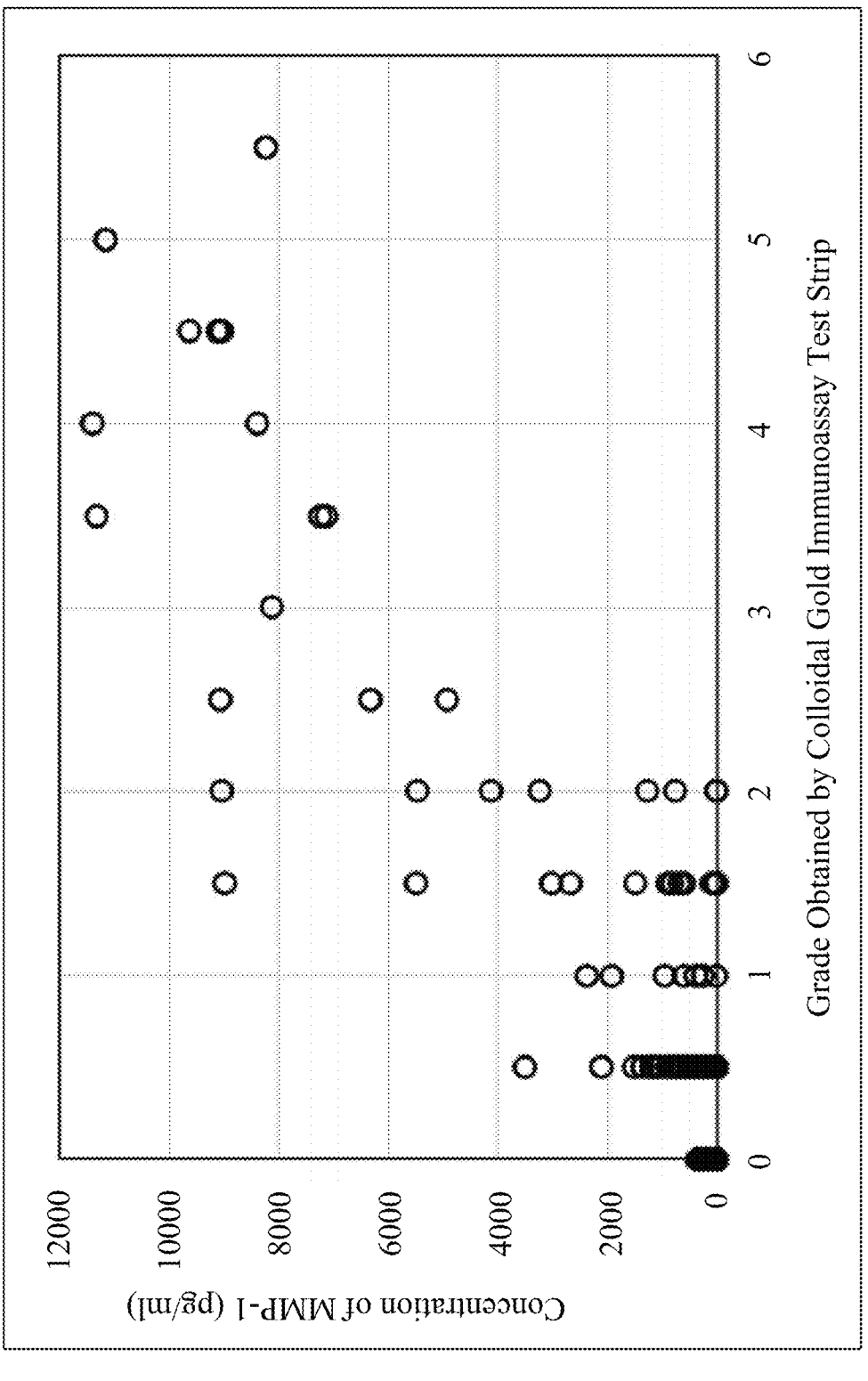
FIG. 4 illustrates a scatter diagram of cross comparison between a colloidal gold immunoassay test strip and an enzyme immunoassay reagent kit in one embodiment of the present disclosure.

FIG. 4 showed that the results of the colloidal gold immunoassay test strip and the results of the enzyme immunoassay were positively correlated, and a correlation analysis result was R=0.871 (p<0.0001). That is, the colloidal gold immunoassay test strip containing the combination C could be used to detect MMP-1 in the clinical saliva samples.

In summary, the embodiments of the present disclosure disclose the detection method effective for detecting endogenous MMP-1 in the clinical samples. The detection method may at least include: the enzyme immunoassay reagent, using No. 4 monoclonal antibody pair (capture antibody: 31-34 strain, and detection antibody: 73-1 strain) and the colloidal gold immunoassay test strip, using the monoclonal antibody pair of the combination C (capture antibody: 1-8A12 strain, and detection antibody: 31-34 strain), and amino acid sequences, main features, and corresponding sequence listing numbers of each monoclonal antibody are shown in Table 7 below.

TABLE 7

Sequence alignment table of 31-34, 73-1 and 1-8A12

| | Sequence | | | | | |
|---|---|---|---|---|---|---|
| | 31-34 | | 73-1 | | 1-8A12 | |
| Main feature | heavy chain variable region | light chain variable region | heavy chain variable region | light chain variable region | heavy chain variable region | light chain variable region |
| CDR1 | SEQ ID NO: 1 | SEQ ID NO: 4 | SEQ ID NO: 7 | SEQ ID NO: 10 | SEQ ID NO: 13 | SEQ ID NO: 16 |
| CDR2 | SEQ ID NO: 2 | SEQ ID NO: 5 | SEQ ID NO: 8 | SEQ ID NO: 11 | SEQ ID NO: 14 | SEQ ID NO: 17 |
| CDR3 | SEQ ID NO: 3 | SEQ ID NO: 6 | SEQ ID NO: 9 | SEQ ID NO: 12 | SEQ ID NO: 15 | SEQ ID NO: 18 |

Embodiment 4. Compare with Detection Result of Control Group

In the development processes of Embodiments 2 to 3, several control groups were also used as the capture antibodies for each detection, and the self-produced 1-8A12 was used as the detection antibody, and detection results were compared and analyzed simultaneously. The antibodies of the control groups are listed in Table 8, which includes a commercially available antibody (No. 7), polyclonal antibodies (No. 1 to 4) produced using MMP-1 peptide fragments as immunogen, polyclonal antibodies (No. 5 to 6) produced using protease-inactive MMP-1 as antigen, and other mouse monoclonal antibodies (No. 8 to 16) produced using protease-inactive MMP-1 as immunogen, a total of 16 antibodies.

TABLE 8

Preparation process information table of antibodies of control group

| No. | Name | Immunogen (amino acid fragment) | Species |
|---|---|---|---|
| 1 | REGA_C | A.A. 101-114 | rabbit |
| 2 | REGA_D | A.A. 253-268 | rabbit |
| 3 | MMP1-10 | A.A. 104-117 | rat |
| 4 | MMP1-11 | A.A. 456-469 | rat |
| 5 | MMP1-R | A.A. 20-469 | rabbit |
| 6 | MMP1-L | A.A. 20-469 | rabbit |
| 7 | MAB901 | A.A. 20-469 | mouse |
| 8 | 1-3E3 | A.A. 20-469 | mouse |
| 9 | 3-1C2 | A.A. 20-469 | mouse |
| 10 | 6-2D2 | A.A. 20-469 | mouse |
| 11 | 7-2I9 | A.A. 20-469 | mouse |
| 12 | 8-2F11 | A.A. 20-469 | mouse |

TABLE 8-continued

| | | Preparation process information table of antibodies of control group | | |
|---|---|---|---|---|
| No. | Name | Immunogen (amino acid fragment) | Species | |
| 13 | 10-4A5 | A.A. 20-469 | mouse | |
| 14 | 11-3F10 | A.A. 20-469 | mouse | |
| 15 | 12-1C11 | A.A. 20-469 | mouse | |
| 16 | 16-2A11 | A.A. 20-469 | mouse | |

Note:
A.A. in the table represents amino acid

Comparison results showed that most of the antibodies could effectively bind to human recombinant MMP-1 in the stage of direct ELISA, but when entering the pairing process, non-specific binding of many pairs was too high, and sensitivities thereof were generally insufficient. In the pair of the control group as the capture antibody and the self-produced antibody as the detection antibody, the best pair was the commercially available antibody MAB901 with 1-8A12-HRP; however, its standard concentration curve range (Table 9A) and its efficacy in detecting MMP-1 in saliva samples (Table 9B) were inferior to those of the self-produced antibody pairs. Therefore, the pairs screened out in the embodiments of the present disclosure were more sensitive than the antibody pairs that the capture antibody using the commercially available antibody, other monoclonal antibodies produced using protease-inactive MMP-1 as immunogen, or polyclonal antibodies using MMP-1 fragments as immunogen.

TABLE 9A

| | Comparison table between standard concentration curve range of control group and values of self-screening antibody pairs | |
|---|---|---|
| Concentration (ng/ml) | OD value | |
| 10 | 2.336 | |
| 5 | 1.193 | |

TABLE 9A-continued

| | Comparison table between standard concentration curve range of control group and values of self-screening antibody pairs | | | | |
|---|---|---|---|---|---|
| Concentration (ng/ml) | OD value | | | | |
| 2.5 | 0.544 | 2.332 | 2.506 | 2.639 | 0.783 |
| 1.25 | 0.258 | | | | |
| 0.625 | 0.119 | 0.598 | 0.846 | 1.124 | 0.194 |
| 0.313 | 0.056 | | | | |
| 0.156 | 0.027 | 0.131 | 0.205 | 0.274 | 0.045 |
| Pairing number | N/A | No. 2 | No. 4 | No. 5 | No. 10 |
| Capture antibody | MAB 901 | 1-8A12 | 31-34 | 73-1 | 6-2 |
| Detection antibody | 1-8A12 | 6-2 | 73-1 | 6-2 | 20-4 |

TABLE 9B

| | Comparison table of results of control group and self-screened antibody pairs for detecting saliva samples | | | | | |
|---|---|---|---|---|---|---|
| Sample number | Concentration (pg/ml) | OD value | | | | |
| 1 | 14821.9 | 2.688 | 2.899 | 3.011 | 2.878 | 2.994 |
| 2 | 5041.1 | 0.883 | 2.682 | 2.66 | 2.769 | 2.05 |
| 3 | 1503.2 | 0.11 | 0.868 | 0.981 | 1.55 | 0.326 |
| 4 | 6.4 | −0.019 | 0.007 | 0.015 | 0.015 | 0.006 |
| 5 | 285.6 | 0.045 | 0.266 | 0.296 | 0.538 | 0.081 |
| 6 | 27.1 | 0.003 | 0.059 | 0.062 | 0.126 | 0.029 |
| 7 | 120.6 | 0.006 | 0.145 | 0.152 | 0.285 | 0.053 |
| 8 | 0 | −0.01 | 0.013 | 0.025 | 0.017 | 0.009 |
| Pairing number | N/A | No. 2 | No. 4 | No. 5 | No. 10 | |
| Capture antibody | MAB 901 | 1-8A12 | 31-34 | 73-1 | 6-2 | |
| Detection antibody | 1-8A12 | 6-2 | 73-1 | 6-2 | 20-4 | |

Although the present invention has been described in considerable detail with reference to certain embodiments thereof, other embodiments are possible. Therefore, the spirit and scope of the appended claims should not be limited to the description of the embodiments contained herein

What is claimed is:

1. A monoclonal antibody, comprising:

a monoclonal antibody A, wherein a heavy chain variable region sequence of the monoclonal antibody A comprises amino acid sequences of SEQ ID NOs: 1, 2, and 3, and a light chain variable region sequence of the monoclonal antibody A comprises amino acid sequences of SEQ ID NOs: 4, 5, and 6;

a monoclonal antibody B, wherein a heavy chain variable region sequence of the monoclonal antibody B comprises amino acid sequences of SEQ ID NOs: 7, 8, and 9, and a light chain variable region sequence of the monoclonal antibody B comprises amino acid sequences of SEQ ID NOs: 10, 11, and 12; or a monoclonal antibody C, wherein a heavy chain variable region sequence of the monoclonal antibody C comprises amino acid sequences of SEQ ID NOs: 13, 14, and 15, and a light chain variable region sequence of the monoclonal antibody C comprises amino acid sequences of SEQ ID NOs: 16, 17, and 18.

2. A polynucleotide, wherein the polynucleotide encodes the full length of the monoclonal antibody A, the full length of monoclonal antibody B, or the full length of the-monoclonal antibody C of claim 1, or has a sequence complementary to a nucleotide sequence that encodes the full length of the monoclonal antibody A, the full length of the-monoclonal antibody B, or the full length of monoclonal antibody C of claim 1.

3. A detection kit, wherein the detection kit comprises a monoclonal antibody A, wherein the monoclonal antibody A comprises:

a heavy chain variable region comprising amino acid sequences of SEQ ID NOs: 1, 2, and 3; and a light chain variable region comprising amino acid sequences of SEQ ID NOs: 4, 5, and 6.

4. The detection kit of claim 3, wherein the detection kit further comprises an enzyme immunoassay reagent kit, a colloidal gold immunoassay test strip or a combination thereof.

5. The detection kit of claim 4, wherein the enzyme immunoassay reagent kit comprises:

a monoclonal antibody B, wherein the monoclonal antibody B comprises:

a heavy chain variable region comprising amino acid sequences of SEQ ID NOs: 7, 8, and 9; and a light chain variable region comprising amino acid sequences of SEQ ID NOs: 10, 11, and 12.

6. The detection kit of claim 5, wherein the monoclonal antibody B is linked to a chromogenic group.

7. The detection kit of claim 4, wherein the colloidal gold immunoassay test strip comprises:

a monoclonal antibody C, comprising:

a heavy chain variable region comprising amino acid sequences of SEQ ID NOs: 13, 14, and 15; and a light chain variable region comprising amino acid sequences of SEQ ID NOs: 16, 17, and 18.

8. The detection kit of claim 4, wherein the colloidal gold immunoassay test strip further comprises the monoclonal antibody A, and the monoclonal antibody A in the colloidal gold immunoassay test strip is linked to a gold particle.

9. A method for detecting matrix metalloproteinase-1 in vitro, comprising:

detecting matrix metalloproteinase-1 in a sample using the detection kit of claim 4, wherein when the detection kit comprises the colloidal gold immunoassay test strip, using the detection kit of claim 7 comprises adding the sample to a colloidal gold pad containing a detection antibody-gold particle conjugate, wherein the detection antibody-gold particle conjugate comprises the monoclonal antibody A, and wherein when the detection kit comprises the enzyme immunoassay reagent kit, using the detection kit of claim 7 comprises performing a sandwich enzyme-linked immunosorbent assay with the monoclonal antibody A as a capture antibody.

10. The method of claim 9, wherein the sample comprises a body fluid or a blood.

11. The method of claim 10, wherein the body fluid comprises an oral secretion or a respiratory secretion.

12. The detection kit of claim 7, wherein the colloidal gold immunoassay test strip further comprises the monoclonal antibody A, and the monoclonal antibody A in the colloidal gold immunoassay test strip is linked to a gold particle.

* * * * *